US012605401B2

(12) United States Patent
Zhou et al.

(10) Patent No.: US 12,605,401 B2
(45) Date of Patent: *Apr. 21, 2026

(54) POLYMERS, COMPOSITIONS AND METHODS FOR TREATING HYPERURICEMIA

(71) Applicant: WATERSTONE PHARMACEUTICALS (WUHAN) CO., LTD., Wuhan (CN)

(72) Inventors: Youcheng Zhou, Wuhan (CN); Tongtong Li, Wuhan (CN); Minglong Hu, Wuhan (CN); Yan Li, Wuhan (CN); Kang Bie, Wuhan (CN); Ying Liang, Wuhan (CN); Jian Cui, Wuhan (CN); Faming Zhang, Wuhan (CN)

(73) Assignee: WATERSTONE PHARMACEUTICALS (WUHAN) CO., LTD., Wuhan (CN)

( * ) Notice: Subject to any disclaimer, the term of this patent is extended or adjusted under 35 U.S.C. 154(b) by 920 days.

This patent is subject to a terminal disclaimer.

(21) Appl. No.: 17/747,006

(22) Filed: May 18, 2022

(65) Prior Publication Data

US 2023/0102864 A1      Mar. 30, 2023

Related U.S. Application Data

(63) Continuation of application No. PCT/CN2021/114310, filed on Aug. 24, 2021.

(51) Int. Cl.
*A61K 31/787* (2006.01)
*A61P 19/06* (2006.01)
*C08F 279/00* (2006.01)

(52) U.S. Cl.
CPC ............ *A61K 31/787* (2013.01); *A61P 19/06* (2018.01); *C08F 279/00* (2013.01)

(58) Field of Classification Search
CPC ....... A61K 31/787; A61P 19/06; C08F 279/00
See application file for complete search history.

(56) References Cited

U.S. PATENT DOCUMENTS

| | | | | |
|---|---|---|---|---|
| 2002/0042395 A1* | 4/2002 | Hadvary | ................ | A61K 31/00 514/60 |
| 2002/0187120 A1* | 12/2002 | Holmes-Farley | .... | A61K 31/785 424/78.31 |
| 2003/0039627 A1* | 2/2003 | Holmes-Farley | ......... | A61P 3/00 424/78.35 |

FOREIGN PATENT DOCUMENTS

| | | |
|---|---|---|
| CN | 1503676 | 6/2004 |
| CN | 1511039 | 7/2004 |
| CN | 101043878 | 9/2007 |
| CN | 101743012 A | 6/2010 |
| WO | 2005032563 | 4/2005 |
| WO | 2010151439 A1 | 12/2010 |

OTHER PUBLICATIONS

Draft Guidance on Colesevelam Hydrochloride Nov. 2021, Revision History: Recommended Aug. 2010; Revised Jun. 2011, Mar. 2012, Jun. 2013, Jan. 2016, Sep. 2019, Nov. 2021 Unique Agency Identifier: PSG_022362. (Year: 2010).*
https://products.sanofi.us/sevelamer_hydrochloride/sevelamer_hydrochloride.pdf (Year: 2000).*
International Search Report.
CAS Registry No. 156-83-2 Nov. 16, 1984(Nov. 16, 1984).
CAS Registry No. 1541141-84-7 Feb. 10, 2014(Feb. 10, 2024).
CAS Registry No. 921852-48-4 Feb. 19, 2007(Feb. 19, 2007).
First Office Action dated Nov. 30, 2025 received in corresponding patent family application No. CN202180005151.4. English translation attached.

* cited by examiner

*Primary Examiner* — Blessing M Fubara

(57) ABSTRACT

The disclosure provides small molecule compounds, polymers, and compositions thereof, as well as methods for preparing such polymers and compositions. Also provided is a method of using the polymers or compositions thereof for binding uric acid or precursor thereof, and/or for treating hyperuricemia, gout, and/or diseases caused by hyperuricemia.

20 Claims, 3 Drawing Sheets

POLYMERS, COMPOSITIONS AND METHODS FOR TREATING HYPERURICEMIA

CROSS-REFERENCE TO RELATED APPLICATIONS

The present application is a continuation of International Patent Application No. PCT/CN2021/114310, filed on Aug. 24, 2021, the entire content of which is incorporated herein by its reference.

FIELD

The present invention relates to polymers and compositions containing such polymers, and methods of using such polymers/compositions for binding uric acid and/or for treating hyperuricemia, gout, and/or diseases caused by hyperuricemia. In addition, certain small molecule compounds are disclosed, which can be used as a reagent.

BACKGROUND

The prevalence of gout is approximately 1.3 to 3.7 percent of the general population. Individuals suffering from gout excrete approximately 40 percent less uric acid, the final breakdown product of purine degradation, than nongouty individuals for any given plasma urate concentrations. Hyperuricemia is formed when the uric acid metabolism of the human body is disturbed, resulting in excessive uric acid production or reduced excretion. The diagnostic index of hyperuricemia is usually that the female blood uric acid level is greater than 6 mg/dl (360 μM), and the male blood uric acid level is greater than 7 mg/dl (420 μM). The main clinical features of gout are hyperuricemia, recurrent acute and chronic attacks of gout caused by hyperuricemia, arthritis, joint deformities, uric acid urinary stones, which cause damage to the kidneys, cause interstitial nephritis, and renal failure.

Current treatments for gouty arthritis include colchicine, anti-inflammatory drugs, and intraarticular glucocorticoids. However, the most effective of these, colchicine administered orally, cannot be tolerated by 80 percent of people because of side effects.

The invention relates to a treatment for gout in an individual with a polymer structurally defined in the claims that binds to uric acid or to a precursor thereof, such as purine. The invention is effective for both treatment and prevention of gout, hyperuricosuria, uric acid nephropathy. Polymers that bind uric acid may also have utility in lowering uric acid levels in a patient at risk of developing coronary heart disease.

Therefore, there exists a great deal of interest in developing new drugs for lowering uric acid and/or for treating hyperuricemia, gout, and/or diseases caused by hyperuricemia.

BRIEF SUMMARY

The present disclosure provides small molecule compounds, polymers (e.g., polytriallylamine and grafted polytriallylamine), and compositions thereof. Also provided are the use of the small molecule compounds, polymers, or compositions described herein for the manufacture of a medicament for binding uric acid or urate, and/or the medicament for the treatment of hyperuricemia, gout, and/or diseases caused by hyperuricemia.

In one aspect, the present disclosure provides a grafted polytriallylamine comprising polytriallylamine, an anion, and a moiety that binds to uric acid or precursor thereof, wherein the moiety is linked to an tertiary amine of the polytriallylamine. In some embodiments, the moiety is selected from the group consisting of a derivative thereof, and any combination thereof. In some embodiments, the moiety is In some embodiments, the anion is selected from the group consisting of $Br^-$, $Cl^-$, $HCO_3^-$ and $CO_3^{2-}$. In some embodiments, the anion is $HCO_3^-$. In some embodiments, the grafted polytriallylamine is 4-N-(6-hexyl)-pyrimidine-2,4,6-triamine grafted polytriallylamine bicarbonate.

In some embodiments, the grafted polytriallylamine is characterized by an average adsorption of uric acid of about 1.0 mmol/g. In some embodiments, the grafted polytriallylamine is characterized by a glass transition temperature in a range of 85-95° C. In some embodiments, the mole percentage of the moiety to the tertiary amine is greater than 35% or in a range of 30% to 70%. In some embodiments, the mole percentage is about 50%. It is also contemplated that the grafted polytriallylamine can be characterized by two or more features recited herein.

In another aspect, provided here is a process of synthesizing polytriallylamine. In some embodiments, the process comprises (1) adding triallylamine to concentrated HCl at a temperature less than 15° C. to prepare hydrochloride triallylamine in an aqueous solution; and (2) mixing the hydrochloride triallylamine with 2,2'-Azobis(2-amidinopropane)

dihydrochloride at an elevated temperature to yield polytriallylamine. In some embodiments, the process comprises (1) adding triallylamine to concentrated HCl at a temperature less than 15° C. to prepare hydrochloride triallylamine in an aqueous solution; (2) mixing the hydrochloride triallylamine with 2,2'-Azobis(2-amidinopropane) dihydrochloride to obtain an aqueous phase; and (3) providing an organic phase to mix with the aqueous phase under nitrogen protection at an elevated temperature to yield polytriallylamine in a mixture. Any composition comprising polytriallylamine produced by the process described herein is contemplated.

In some embodiments, provided is a process of making 4-N-(6-hexyl)-pyrimidine-2,4,6-triamine grafted polytriallylamine bicarbonate, comprising: (1) polymerizing triallylamine to yield polytriallylamine; and (2) reacting 4-N-(6-bromo-hexyl)-pyrimidine-2,4,6-triamine hydrobromide with the polytriallylamine at an elevated temperature.

Also provided is a pharmaceutical composition comprising the grafted polytriallylamine described herein; and a pharmaceutically acceptable excipient, diluent, or carrier.

Further provided is a method of treating a condition associated with an elevated serum uric acid level comprising administering to a subject in need thereof the grafted polytriallylamine or the pharmaceutical composition described herein. In some embodiments, the grafted polytriallylamine or the pharmaceutical composition is administered orally.

Other features and advantages will be apparent from the following description of the certain embodiments thereof and from the claims.

Other aspects of the present disclosure relate to a method for binding uric acid or precursor thereof, and thus lowering uric acid level in a subject in need. In some embodiments, the polymers or compositions described herein are used in a method for treating hyperuricemia, gout, and/or diseases caused by hyperuricemia.

DESCRIPTION OF THE DRAWINGS

The present application can be best understood by reference to the following description taken in conjunction with the accompanying figures included in the specification.

FIG. 2a shows the level of uric acid (UA), FIG. 2b shows that of creatinine (CREA) and FIG. 2c shows that of urea (UREA).

FIG. 3a shows the level of UA, FIG. 3b shows that of CREA and FIG. 3c shows that of UREA.

DETAILED DESCRIPTION

Figure 1:
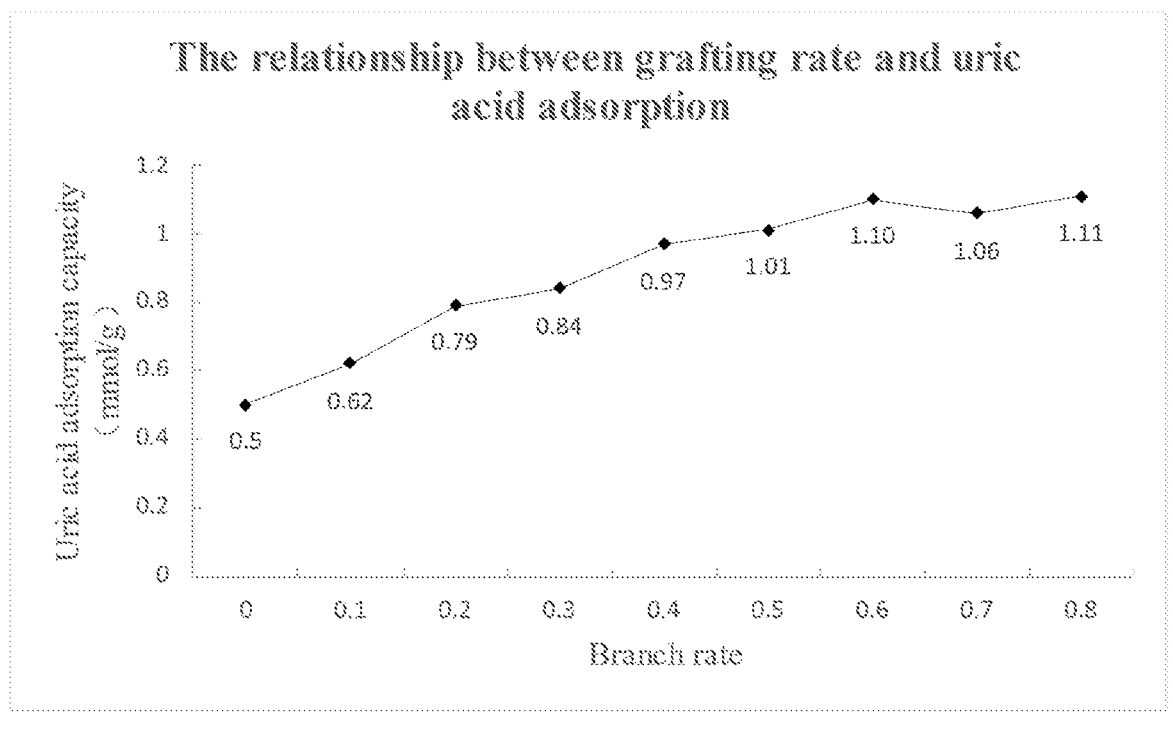
FIG. 1 depicts the relationship between grafting rate and uric acid adsorption of various grafted polytriallylamine.

The present disclosure is based on the inventors' discovery that certain polymers and compositions thereof are effective at binding uric acid.

Unless defined otherwise, all scientific and technical terms are understood to have the same meaning as commonly used in the art to which they pertain. For the purpose of the present disclosure, the following terms are defined.

The term "about" as used herein refers to the usual error range for the respective value readily known to the skilled person in this technical field. Reference to "about" a value or parameter herein includes (and describes) embodiments that are directed to that value or parameter per se. For example, "about x" includes and describes "x" per se. In some embodiments, the term "about" when used in association with a measurement, or used to modify a value, a unit, a constant, or a range of values, refers to variations of +/−2%.

As used herein and in the appended claims, the singular forms "a," "an," and "the" include plural reference unless the context clearly indicates otherwise.

The term "a derivative thereof" refers to a salt thereof, an ester thereof, a free acid form thereof, a free base form thereof, a solvate thereof, a deuterated derivative thereof, a hydrate thereof, an N-oxide thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In some embodiments, "treatment" or "treating" includes an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

In some variations, a "therapeutically effective amount" is at least the minimum concentration required to effect a measurable improvement of a particular disease, disorder, or condition, such as a congenital disorder of glycosylation. A therapeutically effective amount herein may vary according to factors such as the disease state, age, sex, and weight of the subject, and the ability of the compositions of the present disclosure to elicit a desired response in the subject. A therapeutically effective amount is also one in which any toxic or detrimental effects of the lipid compositions of the present disclosure are outweighed by the therapeutically beneficial effects.

Compositions

Provided herein are small molecule compounds, polymers, and compositions thereof, which may be useful in binding uric acid.

Polytriallylamine

In one aspect, the present disclosure relates to polytriallylamine and methods of making polytriallylamine.

In some embodiments, polytriallylamine is synthesized by aqueous polymerization. A method of synthesizing polytriallylamine comprises (1) adding triallylamine to an acid at a temperature less than 15° C. to prepare acidified triallylamine in an aqueous solution; (2) mixing the acidified triallylamine with an azo type initiator at an elevated temperature to yield polytriallylamine. In some embodiments, the acid is a concentrated HCl or sulfuric acid. Suitable azo type initiators that can be used in accordance with the methods described herein include, but are not limited to, 2,2'-Azobis(2-amidinopropane) dihydrochloride, 2,2'-Azobis(2-methylpropionamidine)dihydrochloride (AIBA), Azobisisobutyronitrile (AIBN), and 2,2'-Azobis[2-(2-imidazolin-2-yl)propane] dihydrochloride. In some embodiments, the azo type initiator is 2,2'-Azobis(2-amidinopropane) dihydrochloride. Other suitable initiators such as Potassium persulfate and ammonium persulfate can be used as well.

In some embodiments, the method comprises (1) adding triallylamine to concentrated HCl at a temperature less than 15° C. to prepare hydrochloride triallylamine in an aqueous solution; and (2) mixing the hydrochloride triallylamine with 2,2'-Azobis(2-amidinopropane) dihydrochloride at an elevated temperature to yield polytriallylamine.

The pH of the aqueous solution in step (1) can be in a wide range, for example, between 1 and 6. In some embodiments, the pH of the aqueous solution in step (1) is in a range of 2.6 to 3.1. In some embodiments, the pH of the aqueous solution in step (1) is about 3.5, 3.3, 3.1, 3.0, 2.9, 2.8, 2.7, 2.6, 2.5, 2.4, 2.2, or 2.0.

The elevated temperature in step (2) can be in a wide range, for example, between 20° C. and 85° C. In some embodiments, the elevated temperature in step (2) is between 50° C. and 55° C. In some embodiments, the elevated temperature in step (2) is about 60° C., 55° C., 54° C., 53° C., 52° C., 5° C., 50° C., or 45° C.

The method can further include the following steps: (3) crushing the polytriallylamine into particles; (4) dispersing the particles into a mixture comprising methanol and NaOH at room temperature to yield a dispersion; and (5) filtering the dispersion to obtain a solid.

In some embodiments, polytriallylamine is synthesized by inverse emulsion polymerization. A method of synthesizing polytriallylamine comprises (1) adding triallylamine to concentrated HCl at a temperature less than 15° C. to prepare hydrochloride triallylamine in an aqueous solution; (2) mixing the hydrochloride triallylamine with 2,2'-Azobis(2-amidinopropane) dihydrochloride to obtain an aqueous phase; and (3) providing an organic phase to mix with the aqueous phase under nitrogen protection at an elevated temperature to yield polytriallylamine in a mixture.

The pH of the aqueous solution in step (1) can be in a wide range, for example, between 1 and 6. In some embodiments, the pH of the aqueous solution in step (1) is in a range of 2.6 to 3.1. In some embodiments, the pH of the aqueous solution in step (1) is about 3.5, 3.3, 3.1, 3.0, 2.9, 2.8, 2.7, 2.6, 2.5, 2.4, 2.2, or 2.0.

In some embodiments, the elevated temperature in step (3) is between 50° C. and 55° C. In some embodiments, the elevated temperature in step (3) is about 60° C., 55° C., 54° C., 53° C., 52° C., 51° C., 50° C., or 45° C.

The elevated temperature can be further increased to a range of 80° C. and 85° C. In some embodiments, the further elevated temperature is about 90° C., 85° C., 84° C., 83° C., 82° C., 81° C., 80° C., or 75° C.

The organic phase may include suitable organic components such as cyclohexane, toluene and sorbitan monostearate (Span60). In some embodiments, the organic phase comprises toluene and sorbitan monostearate (Span60).

The method can further include (4) filtering the mixture to obtain a solid of polytriallylamine.

The polytriallylamine produced here is characterized by a glass transition temperature (Tg). The glass transition temperature of polytriallylamine is in a range of 140-160° C. In some embodiments, the glass transition temperature is about 140° C., 145° C., 150° C., 155° C., or 160° C.

In some embodiments, the polytriallylamine produced here has an average particle size greater than 3 μm, e.g., d(0.01): 3 μm. It would be appreciated that the polymers described here do not degrade under the physiological conditions and are generally not absorbed from the gastrointestinal tract.

Also provided are any compositions comprising polytriallylamine produced by the methods described herein.

Pyrimidine-2,4-Diamine and Analogs

In another aspect, described herein are an analog of pyrimidine-2,4-diamine. The analog of pyrimidine-2,4-diamine can be used as reagents to graft a moiety onto a polymeric network, for example, polytriallylamine. Without being bound to any particular theory, it is believe that the moiety grafted onto polytriallylamine can form hydrogen bonds with uric acid and thus improve the adsorption of uric acid of the grafted polytriallylamine.

In some embodiments, the analog is selected from the group consisting of 6-chloropyrimidine-2,4-diamine, 4-N-(6-bromo-hexyl)pyrimidine-2,4,6-triamine N-(6-bromo-hexyl)pyrimidine-2,4,6-triamine Grafted Polytriallylamine Other aspects of the present disclosure relate to a polymer comprising a polymeric network of polytriallylamine and a moiety grafted onto the polymeric network. In some embodiments, the polymer comprises polytriallylamine, an anion, and a moiety that binds to uric acid or precursor thereof, wherein the moiety is linked to the tertiary amine of polytriallylamine. In some embodiments, the polymer is 4-N-(6-hexyl)-pyrimidine-2,4,6-triamine grafted polytriallylamine bicarbonate.

The moiety can bind to uric acid. In some embodiments, the moiety is selected from the group consisting of

7

-continued a derivative thereof, and any combination thereof. In some embodiments, the moiety is In some embodiments, the moiety is In some embodiments, the anion is selected from the group consisting of Br⁻, Cl⁻, HCO₃⁻ and CO₃²⁻. In some embodiments, the anion is HCO₃⁻.

The grafted polytriallylamine described exhibits high adsorption of uric acid or precursor thereof. In some embodiments, the grafted polytriallylamine is characterized by an average adsorption of uric acid in a range from about 0.1 mmol/g to about 10 mmol/g. In some embodiments, the average adsorption of uric acid is in a range from about 0.1 mmol/g to about 0.2 mmol/g, from about 0.2 mmol/g to about 0.5 mmol/g, from about 0.5 mmol/g to about 1 mmol/g, from 1 mmol/g to about 5 mmol/g, from about 5 mmol/g to about 10 mmol/g. In some embodiments, the average adsorption of uric acid is about 0.1 mmol/g, about 0.2 mmol/g, about 0.3 mmol/g, about 0.5 mmol/g, about 1 mmol/g, or about about 2 mmol/g. The high adsorption of uric acid or precursor thereof can enable the administration of a low dose of the grafted polytriallylamine or a composition comprising the grafted polytriallylamine.

Depending on molar ratios of an analog of pyrimidine-2, 4-diamine to polytriallylamine used in the synthesis, the molar percentages of the moiety to the tertiary amine in polytriallylamine may vary. In some embodiments, the molar percentage of the moiety to the tertiary amine in polytriallylamine is about or greater than 35%, 45%, or 50%. In some embodiments, the molar percentage is in a range from 30% to 80%, from 35% to 70%, from 35% to 50%, or from 50% to 70%.

The grafted polytriallylamine described here is characterized by a glass transition temperature (Tg). The glass transition temperature of grafted polytriallylamine is in a range of 85-95° C. In some embodiments, the glass transition temperature is about 85° C., 90° C., or 95° C.

In some embodiments, the grafted polytriallylamine described here has an average particle size greater than 3 µm, e.g., d(0.01): 3 µm. It would be appreciated that the polymers described here do not degrade under the physiological conditions and are generally not absorbed from the gastro-intestinal tract.

A method of making the grafted polytriallylamine is also disclosed. For example, provided herein is a method of 4-N-(6-hexyl)-pyrimidine-2,4,6-triamine grafted polytriallylamine bicarbonate. The method comprises (1) polymerizing triallylamine to yield polytriallylamine; and (2) reacting 4-N-(6-bromo-hexyl)-pyrimidine-2,4,6-triamine hydrobromide with the polytriallylamine at an elevated temperature.

Grafted polytriallylamine may be produced by the methods described herein. Also provided are any compositions comprising the grafted polytriallylamine produced by the methods described herein.

Pharmaceutical Compositions

Pharmaceutical compositions of the present disclosure contain polymers (e.g., polytriallylamine and grafted polytriallylamine) or compositions thereof as described herein, and appropriate carriers including, for example, pharmaceutically acceptable carriers or diluents.

In some embodiments, carriers include pharmaceutically acceptable carriers, excipients, or stabilizers that are non-toxic to the cell or subject being exposed thereto at the dosages and concentrations employed. Often the physiologically acceptable carrier is an aqueous pH buffered solution. Suitable physiologically acceptable carriers include, for example, buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Suitable formulations include, for example, solutions, injections, inhalants, microspheres, aerosols, gels, ointments, creams, lotions, powders, dry vesicular powders, tablets, and capsules. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Such diluents include, for example, distilled water, buffered water, physiological saline, PBS, Ringer's solution, dextrose solution, and Hank's solution. A pharmaceutical composition or formulation of the present disclosure can further include, for example, other carriers or non-toxic, nontherapeutic, nonimmunogenic stabilizers, and excipients. The compositions can also include additional substances to approximate physiological conditions, such as pH adjusting and buffering agents, toxicity adjusting agents, wetting agents and detergents. A pharmaceutical composition of the present disclosure can also include any of a variety of stabilizing agents, such as an antioxidant for example.

Pharmaceutical compositions of the present disclosure can be suitable for oral or intestinal administration. In some embodiments, the pharmaceutical compositions of are used (e.g., administered to a subject in need of treatment, such as a human individual) by oral administration. For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Dosages and desired concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. For in vivo administration of any of the compositions of the present disclosure, normal dosage amounts may vary from 10 ng/kg up to 100 mg/kg of a subject's body weight per day.

Administration of a composition of the present disclosure can be continuous or intermittent, depending, for example, on the recipient's physiological condition, whether the purpose of the administration is therapeutic or prophylactic, and other factors known to skilled practitioners. It is within the scope of the present disclosure that dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Thus, in some variations, the compositions provided herein may be chronically or intermittently administered to a subject (including, for example, a human) in need thereof. In certain variations, chronic administration is administration of the medicament(s) in a continuous as opposed to acute mode, so as to maintain the initial therapeutic effect (activity) for an extended period of time. In certain variations, intermittent administration is treatment that is not consecutively done without interruption, but rather is cyclic in nature.

Therapeutic Uses

The polymers and compositions described herein can bind to uric acid or precursor thereof. Provided is a method of treating hyperuricemia, gout, and/or diseases caused by hyperuricemia comprising administering the polymers or compositions described herein to a subject in need thereof. The subject can be a mammal. In one embodiment, the subject is a human.

In some embodiments, a method of treating a condition associated with an elevated serum uric acid level comprises administering the polymers or compositions described hereinto a subject in need thereof. The subject's serum uric acid level is lowered after the treatment as compared to the serum uric acid level before the treatment.

In some embodiments, the condition is hyperuricemia or gout. The gout can be server, chronic or acute. In some embodiments, the condition is a disease caused by hyperuricemia. In some embodiments, a method of treating chronic gouty arthritis, uric acid nephropathy, or stone disease comprises administering the polymers or compositions described hereinto a subject in need thereof.

Uric acid is naturally synthesized by xanthine oxidase-catalyzed oxidation of hypoxanthine and xanthine. Accordingly, in some embodiments, the polymers or compositions described herein are administered with a uric acid synthesis inhibitor such as a xanthine oxidase inhibitor. In one embodiment, the xanthine oxidase inhibitor is allopurinol. In another embodiment, the polymers or compositions described herein are administered with a uricosuric agent, which can act directly on the renal tubules to increase excretion of uric acid. In yet another embodiment, additional ingredients, for example, nonsteroidal anti-inflammatory drugs such as colchicine, ingredients for treating other related indications can be administered simultaneously or sequentially with the polymers or compositions described herein.

EXAMPLES

The following Examples are merely illustrative and is not meant to limit any aspects of the present disclosure in any way.

Below is an exemplary reaction scheme for making 4-N-(6-bromo-hexyl)-pyrimidine-2,4,6-triamine hydrobromide. The synthesis is illustrated in Examples 1 and 2.

Below is an exemplary reaction scheme for making a polymer of formula (I-a). The synthesis is illustrated in Examples 3 and 4.

Monomer MW: 137.22
*is an extended polymeric network $^a$ is equal to 0.55
$^b$ is equal to 0.45

Example 1

To a 2 L high-pressure reactor was added 2,4-diamino-6-chloropyrimidine (100 g), 6-amino-1-hexanol (97.3 g), $K_2CO_3$ (143.3 g) and 1 L water, stir and heat the reaction to 140-150° C., react for 24-48 h. Cool the reaction to 70-80° C., transfer the reaction solution to a flask, and cool to 10-15° C. slowly, then stir the mixture at 10-15° C. for 6-12 h. Filter the mixture, rinse the wet cake with 150 mL*2 cold water twice. Dry the wet cake at 60-70° C. for 48 h. To a 2 L flask was added the dried solid (140.0 g), LiBr (216.0 g), and 1.4 L Conc. 48% HBr (aqueous), stir to dissolve. Heat the reaction to 80-85° C., and react for 4-6 h. Then cool the reaction to 0-10° C., dropwise the 545 g Conc. 50% NaOH (aqueous) slowly, and stir at 10-20° C. for 12-18 h. Filter the mixture, take the wet product sample for purity and assay analysis.

Example 2

To a 2 L round bottom flask was added 2,4-diamino-6-chloropyrimidine (100 g), 6-amino-1-hexanol (121.6 g), $K_2CO_3$ (143.3 g) and 900 mL water, stir and heat the reaction to 100-110° C., react for 72-96 h. Cool the reaction to 10-25° C. slowly, continue to stir the mixture at 10-25° C. for 8-12 h. Filter the mixture, rinse the wet cake with 300 mL cold water. Dry the wet cake at 50-60° C. for 24-36 h. The purity of the intermediate product above 98%, and the yield is 80-95%. To a 1 L flask was added the dried solid (100.0 g), LiBr (115.7 g) and 550 mL Conc. 48% HBr (aqueous), protect from light, stir and heat the reaction to 80-85° C., and react for 4-6 h. Then cool the reaction to 10-25° C. within 1-3 h, then stir the mixture at 10-25° C. for 8-12 h. Filter the mixture, slurry the wet cake in 250 mL water for 3-4 h at 10-25° C., then filter the mixture and rinse the wet cake with 100 mL water. Dry the wet cake at 40-45° C. for 24-36 h. The purity of the final product above 97%, the yield is 55-65%.

Example 3

To a 250 mL round bottom flask was added Conc. HCl (36.6 g), stir and cool to about −10° C., dropwise 50.0 g triallylamine slowly below 15° C. Adjust pH to 2.6-3.1 after dropwise over. Heat the solution to 20-25° C., replace the flask with nitrogen 3 times. Dissolve 2.6 g 2,2'-Azobis(2-methylpropionamidine) dihydrochloride (V50) in 15.0 g water, and charge it into the flask by injection. Heat to 50-55° C. and react for about 1-2 h, stop stirring after the reaction solution was gelled, continue keep the temperature at 50-55° C. for 12 h. Crush the polymer gel, and transfer the particles into a flask, add 1.0 L methanol and NaOH (14.6 g), stir for 1-2 h at room temperature. Filter the mixture, and the wet solid was standby application.

Dissolve 173.2 g N-(6-Bromo-hexyl)-pyrimidine-2,4,6-triamine Hydrobromide (Assay: 55.2%) in 1.7 L methanol. Add NaHCO$_3$ (68.8 g) into the solution slowly, filter the mixture after stir for 1-2 h, the filter liquor was standby application. Charge the filter liquor and the wet solid in a flask, stir and heat to 65-70° C., reflux for 48-72 h. Filter the mixture, rinse the wet cake with 600 mL methanol. Slurry the solid in 600 mL 2M NaCl (aqueous) for 1 h, then filter the mixture, and repeat the operation 2-3 times, rinse the solid until the conductivity of the filter liquor below 200 us/cm. Suspending the solid in 600 mL water, adjust the pH of the mixture to about 13.0 with dropwise Conc. 20% NaOH (aqueous). Bubble the suspension mixture with CO$_2$ until the pH reached about 10.0. Then stir for 0.5 h at room temperature, filter the mixture and rinse the solid until the conductivity of the filter liquor below 200 us/cm. Dry the wet product at 55-60° C. for 48 h, crush the product and a yellow solid was obtained.

Example 4

To a 500 mL round bottom flask was added Conc. HCl (72.4 g), stir and cool to about −10-0° C., dropwise 100.0 g Triallylamine slowly below 15° C. Adjust pH to 2.6-3.1 after dropwise over.

Preparation of aqueous phase: Dissolve 5.34 g 2,2'-Azo-bis(2-methylpropionamidine) dihydrochloride (V50) in 48.0 g water, make a 10% V50 aqueous solution, charge the solution into the Triallylamine Hydrochloric solution, stir at 5-15° C. for 10-20 min and the aqueous phase was prepared.

Preparation of organic phase: To a 1 L flask with mechanical stirrer was added 450 mL Toluene and 3.4 g Sorbitan monostearate (Span60). Purge the flask with nitrogen 3 times, then protect the reaction with slight nitrogen flow. Stir and heat to 40-50° C., the organic phase was clear after stir for 10-20 min.

Adjust the rate of stirrer to 400 RPM, charge the aqueous phase into the organic phase under nitrogen protection, then heat the mixture to 55-60° C., stir at 55-60° C. for 10-15 h. Heat the mixture to 80-85° C. and stir for 4-5 h. Cool the reaction to 55-65° C., filter the mixture, rinse the wet cake with 500 mL hot water. Slurry the wet solid in 1 L water at 40-55° C. for 0.5-1 h, filter the mixture, and repeat the operation 3 times. Suspending the wet solid in 1 L water, stir and add 60 g 50% NaOH (aqueous), filter the mixture after stir for 2-3 h at room temperature, Suspending the wet solid in 300 mL 10% NaOH (aqueous), heat to 90-95° C., filter the mixture after stir for 3-4 h. Slurry the wet solid in 1 L water for 0.5-1 h, filter the mixture and repeat the operation once. Rinse the wet cake with water until the pH of the filter liquor reach about 7, the conductivity of the filter liquor below 100 us/cm. Dry the wet solid at 45-55° C. for 24-36 h under vacuum, a white-off polytriallylamine was obtained, and the yield is 50-70%.

To a 250 mL round bottom flask was added 80 mL methanol and 1.8 g NaOH, cool to 0-10° C. after the NaOH was dissolved. Add N-(6-Bromo-hexyl)-pyrimidine-2,4,6-triamine Hydrobromide (13.4 g) into the flask slowly, stir at 0-10° C. for 0.5-1 h. Add 10.0 g polytriallylamine, purge the flask with nitrogen and slight nitrogen protection. Heat to 65-70° C., reflux for 24-48 h. Cool the reaction to 30-40° C., filter the mixture and rinse the wet solid with 20 mL methanol. Slurry the wet solid in 80 mL methanol, stir at 30-40° C. for 0.5-1 h, filter the mixture and rinse the wet solid with 20 mL methanol, repeat the slurry operation once. Suspending the wet solid in 100 mL 8% NaHCO$_3$, stir at 35-40° C. for 0.5-1 h, filter the mixture and rinse the wet solid with 20 mL water, repeat the slurry operation 5 times. Suspending the wet solid in 100 mL water, stir at 25-35° C. for 0.5-1 h, filter the mixture and rinse the wet solid with 20 mL water, repeat the slurry operation 2 times. Rinse the wet cake with water until the pH of the filter liquor reach about 7, the conductivity of the filter liquor below 100 us/cm. Dry the wet solid at 40-50° C. for 24-36 h under vacuum, a yellow polymer API was obtained, and the yield is about 90%.

Example 5

Solutions were prepared as follows:

Diluent: water.

Blank solution: same as diluent.

Phosphate buffer (pH6.8) was composed of the following: KH$_2$PO$_4$ 0.68 g/L, 0.24 g/L NaHCO$_3$, 0.32 g/L NaOH, and adjust pH to 6.8 with phosphoric acid.

Uric acid solution (2.1 mmol/L): uric acid (353 mg) was dissolved into 1 L Phosphate buffer pH6.8.

Linear stock solution: accurately take 5 ml of Uric acid solution (2.1 mmol/L) to a 50 ml volumetric flask, dilute to volume with sample solution, and mix.

Standard Linear solution: identify five 10 ml volumetric flasks by the numbers 1, 2, 3, 4, and 5. In that order pipet into the flasks 1, 3, 5, 8, and 10 ml respectively, of Linear stock solution. Dilute with water to volume, and mix.

Sample solution: Take about 100 mg of polymer sample, place it in a 250 ml Erlenmeyer flask, add 100 ml of uric acid binding solution, water bath at 37° C.±2° C., stir with magnet for 2 h, shake evenly, measure the solution and filter, precise measurement continued 1 ml of filtrate, put in a 10 ml measuring flask, and dilute to the mark with water.

The chromatographic system used is described below.

| Chromatographic system | |
| --- | --- |
| HPLC | Agilent 1260 or equivalent |
| Column | ACE Excel 5 C8, |
| | 4.6 mm × 150 mm, 5 μm |
| Detection wavelength | 293 nm, no reference |
| Flow rate | 1.0 ml/min |
| Column temperature | 30° C. |
| Injection volume | 10 μl |
| Run time | 8 min |
| Mobile phase | A: 0.05% phosphoric acid solution |
| | (Take 0.5 ml phosphoric acid, |
| | add 1 L purified water, and mix.) |
| | B: Methanol |
| Isocratic elution | mobile phase A- mobile |
| | phase B (95:5) |

A blank solution, the Standard Linear solution and a sample solution were injected respectively.

Blank solution has no interference with uric acid impurity peak. On ruled coordinate paper, plot the observed instrument readings as the ordinate, and the concentrations, in μmol per liter, of uric acid as the abscissa. The linear correlation coefficient should not be less than 0.999.

Uric acid adsorbed on the polymers was calculated by the formula:

$$\frac{(C_0 - C_1) \times V}{W}$$

in which C$_0$ is the concentration, in μmol per lite, of uric acid in 100 mL of uric acid solution (2.1 mmol/L) before exchange; $C_1$ is the concentration remaining after adsorption in µmol per lite, V is 100 ml; and W is the weight, in gram, of polymers taken, expressed on the anhydrous basis.

To eight 250 mL round bottom flask were added 80 mL methanol and (0.35 g, 0.7 g, 1.05 g, 1.4 g, 1.75 g, 2.1 g, 2.45 g, 2.7 g) NaOH respectively, cool to 0-10° C. after the NaOH was dissolved. Add 4-N-(6-Bromo-hexyl)-pyrimidine-2,4,6-triamine hydrobromide (2.69 g (0.1 eq), 5.38 g (0.2 eq), 8.07 g (0.3 eq), 10.76 g (0.4 eq), 13.45 g (0.5 eq), 16.14 g (0.6 eq), 18.83 g (0.7 eq), and 21.52 g (0.8 eq)) into the flask respectively, stir at 0-10° C. for 0.5-1 h. Add 10.0 g polytriallylamine respectively, purge the flask with nitrogen and slight nitrogen protection. Heat to 65-70° C., reflux for 24-48 h. Cool the reaction to 30-40° C., filter the mixture and rinse the wet solid with 20 mL methanol. Slurry the wet solid in 80 mL methanol, stir at 30-40° C. for 0.5-1 h, filter the mixture and rinse the wet solid with 20 mL methanol, repeat the slurry operation once. Suspending the wet solid in 100 mL 8% NaHCO₃, stir at 35-40° C. for 0.5-1 h, filter the the chronic modeling method. The modeling method was as follows: rats were given Adenine (100 mg/kg)+Ethambutol (250 mg/kg) by gavage, once a day, for 21 days. Animals in blank group and model group were given equal volume of normal saline by gavage. Animals in positive control group were given positive 10 mg/kg Alloalcohol, once in the first week, once in the second week, once a day for 3 days before sampling in the third week. Animals in other groups were given intragastric administration once a day for 14 consecutive days from the 8th day of modeling. Blood samples were taken at Day 21 after modeling, and serum samples were separated and stored at −80° C. for biochemical detection.

Figure 2A:
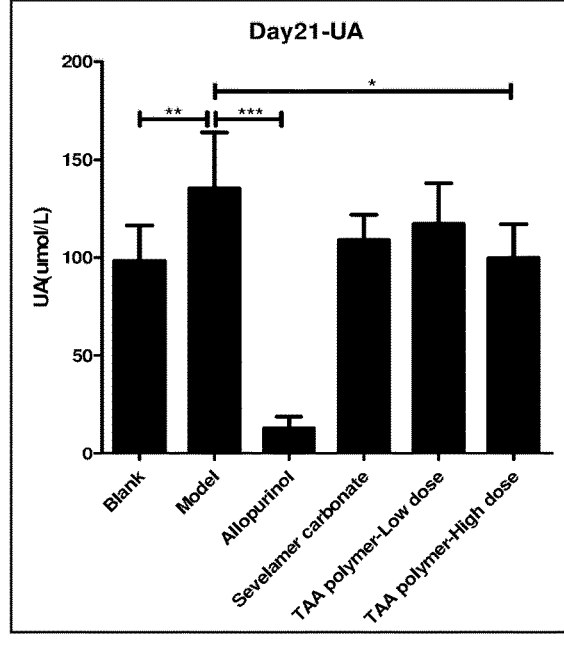
FIGS. 2a, 2b and 2c illustrate results of the first model, in which rats were given adenine (100 mg/kg)+ethylambutol (250 mg/kg) intragastric administration, once a day for consecutive 21 days.
Figure 2B:
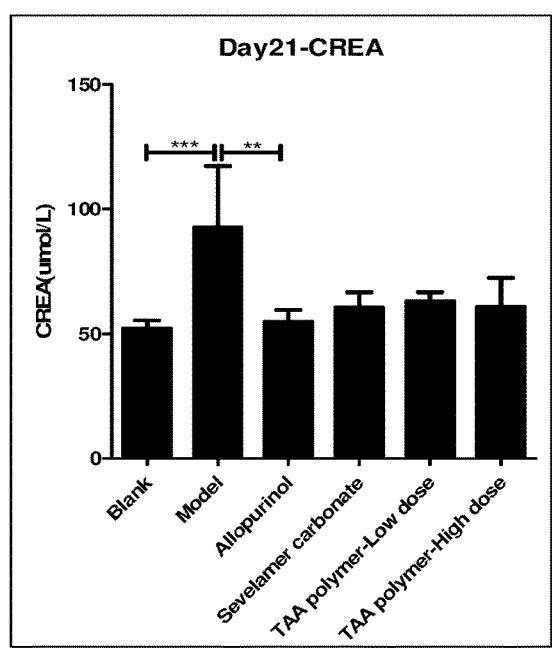
Figure 2C:
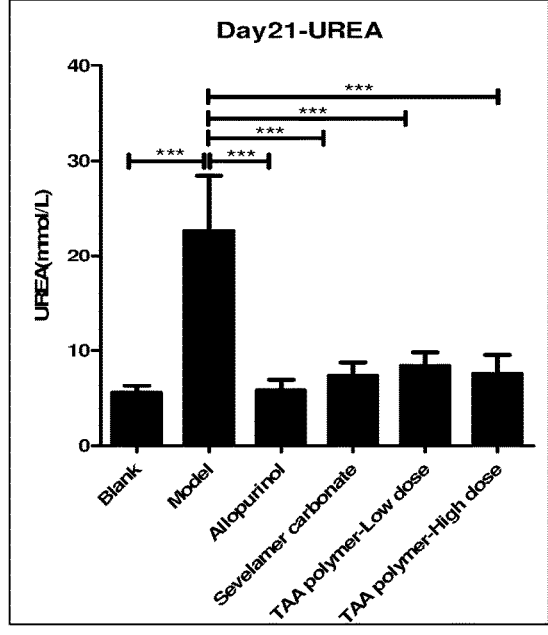
Figure 3A:
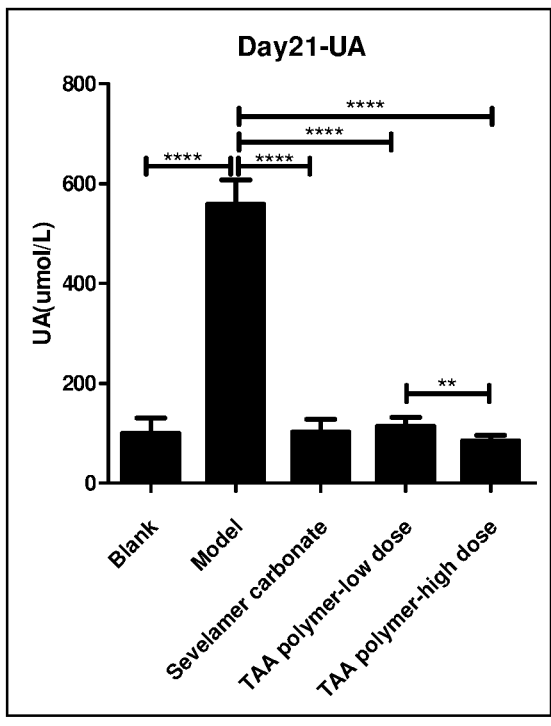
FIGS. 3a, 3b and 3c illustrates results of the second model, in which rats were given adenine 100 mg/kg+ethylambutol 250 mg/kg+yeast powder 7.5 g/kg, once a day for consecutive 21 days.
Figure 3B:
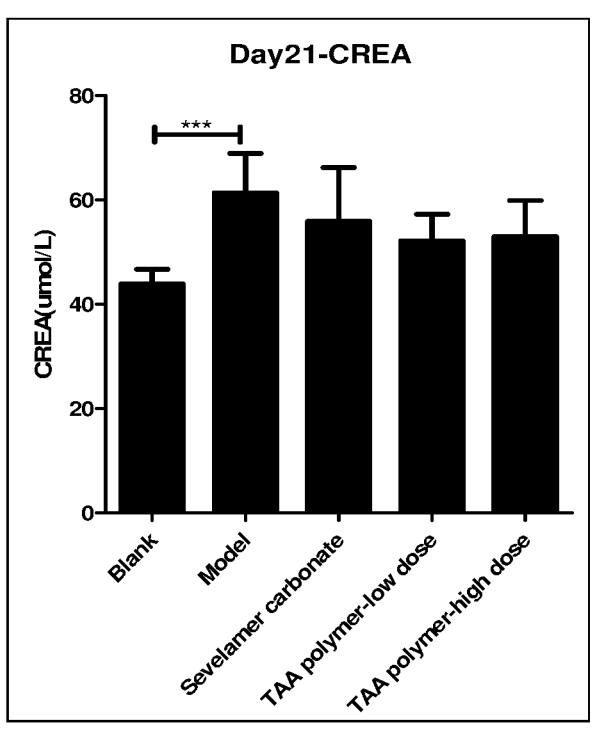
Figure 3C:
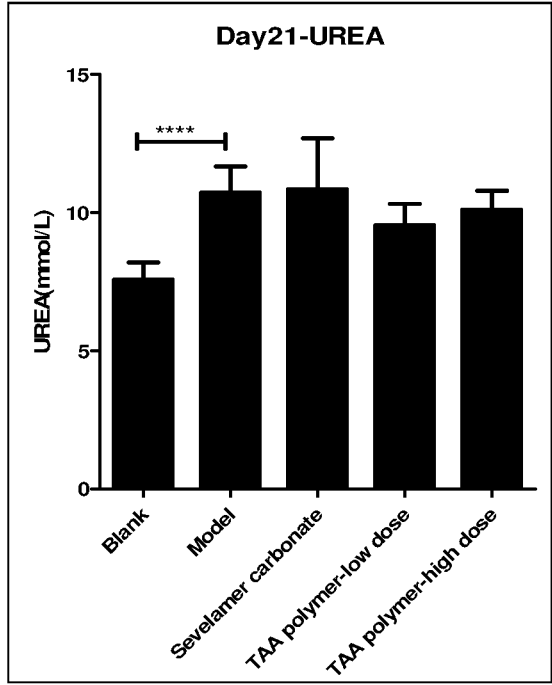

After 21 days of modeling (14 days of drug treatment), blood samples were taken and serum separation was performed to detect three renal functions (UA, CREA and UREA) (See Table 1 and FIGS. 2a, 2b and 2c). Compound 1 is Sevelamer carbonate and Compound 2 is a graft polytriallylamine with 50% molar percentage of the moiety to the tertiary amine in polytriallylamine.

TABLE 1

| | | | Biochemical results after 21 days of modeling (14 days of administration) | | |
|---|---|---|---|---|---|
| Group | Test Article | Dose (mg/kg) | UA (umol/L) | CREA (umol/L) | UREA (mmol/L ) |
| Blank | Vehicle | — | 98.18 ± 18.08 | 52.01 ± 3.22 | 5.57 ± 0.75 |
| Model | Vehicle | — | 135.00 ± 28.91** | 92.62 ± 24.80*** | 22.64 ± 5.77*** |
| Positive | Allopurinol | 10 | 12.88 ± 6.01### | 54.73 ± 4.75## | 5.82 ± 1.10### |
| Compound 1 | Sevelamer carbonate | 250 | 108.80 ± 12.99 | 60.41 ± 6.15 | 7.37 ± 1.39### |
| Compound 2 low-dose | TAA polymer | 50 | 117.00 ± 20.66 | 62.92 ± 3.69 | 8.42 ± 1.39### |
| Compound 2 high-dose | TAA polymer | 250 | 99.65 ± 17.22## | 60.70 ± 11.69 | 7.55 ± 1.99### |

Compared with blank group,
*P < 0.05,
**P < 0.01,
***P < 0.001;
compared with model group,
P < 0.05,
P < 0.01,
P < 0.001.

mixture and rinse the wet solid with 20 mL water, repeat the slurry operation 5 times. Suspending the wet solid in 100 mL water, stir at 25-35° C. for 0.5-1 h, filter the mixture and rinse the wet solid with 20 mL water, repeat the slurry operation 2 times. Rinse the wet cake with water until the pH of the filter liquor reach about 7, the conductivity of the filter liquor below 100 us/cm. Dry the wet solid at 40-50° C. for 24-36 h under vacuum.

The adsorption of uric acid of 4-N-(6-hexyl)-pyrimidine-2,4,6-triamine grafted polytriallylamine bicarbonate is depicted in FIG. 1. As shown, when the mole ratio of 4-N-(6-hexyl)-pyrimidine-2,4,6-triamine to the tertiary amine in polytriallylamine is greater than about 35%, the average adsorption of uric acid is about 1.0 mmol/g.

Example 6

48 rats were randomly divided into 6 groups with 8 rats in each group. The groups were as follows: Blank Group (Vehicle, ig), Model Group (Vehicle, ig), Positive control group (Allopurinol, 10 mg/kg, ig), Compound 1 group (Sevelamer carbonate, 250 mg/kg, ig), Compound 2 low-dose group (TAA polymer, 50 mg/kg, ig), Compound 2 high-dose group (TAA polymer, 250 mg/kg, ig). Except for blank group, rats in other groups were modeled according to It was found that after 21 days of modeling, compared with Blank group, the UA in Model group was significantly higher (P<0.01), and the UA in Allopurinol group was significantly reduced (P<0.001), the UA in Compound 2 high-dose group also significantly reduced (P<0.01).

In addition, after 21 days of modeling, compared with Blank group, CREA and UREA in Model group were significantly higher (P<0.001; respectively). The expression of CREA and UREA was significantly reduced by treatment with Allopurinol (P<0.01, P<0.001; respectively). The low-dose of Compound 2 could significantly reduce the expression of CREA. Compound 1 and High and low doses of Compound 2 and 3 significantly reduced UREA expression (P<0.001 respectively).

In conclusion, the model was successfully established, and kidney damage can occur in the chronic hyperuricemia model rats. The positive drug Allopurinol significantly reduced uric acid. The high dose of the Compound 2 showed significant uric acid lowering effects. In addition, Allopurinol and the both two tested compounds can decrease CREA and UREA, indicating that they have a certain protective effect on the kidney.

Example 7

40 rats were randomly divided into 5 groups with 8 rats in each group. The groups were as follows: Blank Group (Vehicle, ig), Model Group (Vehicle, ig), Compound 1 group (Sevelamer carbonate, 100 mg/kg, ig) Compound 2 low-dose group (TAA polymer, 100 mg/kg, ig), Compound 2 high-dose group (TAA polymer, 1000 mg/kg, ig). Except for blank group, rats in other groups were modeled according to the chronic modeling method. The modeling method was as follows: 100 mg/kg adenine+250 mg/kg ethambutol+7.5 g/kg yeast powder were given to rats by gavage, once a day, for 21 days. Animals in blank group and model group were given equal volume of normal saline by gavage. Animals in other groups were given intragastric administration once a day for 14 consecutive days from the 8th day of modeling. Blood samples were taken at Day 21 after modeling, and serum samples were separated and stored at $-80°$ C. for biochemical detection.

After 21 days of modeling (14 days of drug treatment), blood samples were collected and serum samples were separated to detect three renal functions (UA, CREA and UREA). (See Table 2 and FIGS. $3a$, $3b$ and $3c$).

TABLE 2

Biochemical results after 21 days of modeling (14 days of administration)

| Group | Test Article | Dose (mg/kg) | UA (umol/L) | CREA (umol/L) | UREA (mmol/L) |
|---|---|---|---|---|---|
| Blank | Vehicle | — | $99.67 \pm 30.92$ | $43.89 \pm 2.779$ | $7.572 \pm 0.6343$ |
| Model | Vehicle | — | $558.70 \pm 48.91$*** | $61.34 \pm 7.542$*** | $10.73 \pm 0.9438$*** |
| Compound 1 | Sevelamer carbonate | 100 | $102.40 \pm 26.04$### | $55.87 \pm 10.34$ | $10.85 \pm 1.840$ |
| Compound 2 low-dose | TAA polymer | 100 | $114.30 \pm 17.85$### | $52.15 \pm 5.117$ | $9.542 \pm 0.7760$ |
| Compound 2 high-dose | TAA polymer | 1000 | $84.95 \pm 11.01$### | $52.95 \pm 6.960$ | $10.11 \pm 0.6766$ |

Compared with blank group,
*$P < 0.05$,
**$P < 0.01$,
***$P < 0.001$;
compared with model group,
$P < 0.05$,
$P < 0.01$,
$P < 0.001$.

Compared with blank group, UA, CREA and UREA in model group were significantly increased ($P<0.0001$; $P<0.0001$; $P<0.0001$, respectively). Compared with model group, uric acid was significantly reduced in Compound 1 group, Compound 2 low-dose group and Compound 2 high-dose group ($P<0.0001$; $P<0.0001$; $P<0.0001$, respectively). In addition, a separate comparison was made between the Compound 3 low-dose group and the the Compound 3 high-dose group. There was no statistical difference in CREA and UREA between this two groups ($P>0.05$).

In conclusion, the model was successfully established, and kidney damage can occur in the chronic hyperuricemia model rats. Both the two compounds had obvious effect of lowering uric acid. However, the Compound 1 and 2 had no obvious effect of lowering urea and creatinine.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims.

All references, patent and non-patent, cited herein are incorporated herein by reference in their entireties and for all purposes to the same extent as if each individual publication or patent or patent application was specifically and individually indicated to be incorporated by reference in its entirety for all purposes.

What is claimed is:

1. A grafted polytriallylamine comprising polytriallylamine, an anion, and a moiety that binds to uric acid or precursor thereof, wherein the moiety is linked to a tertiary amine of the polytriallylamine.

2. The grafted polytriallylamine of claim 1, wherein the moiety is selected from the group consisting of -continued a derivative thereof, and any combination thereof.

3. The grafted polytriallylamine of claim 2, wherein the moiety is

4. The grafted polytriallylamine of claim 1, wherein the anion is selected from the group consisting of Br⁻, Cl⁻, $HCO_3^-$ and $CO_3^{2-}$.

5. The grafted polytriallylamine of claim 1, wherein the anion is $HCO_3^-$.

6. The grafted polytriallylamine of claim 1, wherein the grafted polytriallylamine is 4-N-(6-hexyl)-pyrimidine-2,4,6-triamine grafted polytriallylamine bicarbonate.

7. The grafted polytriallylamine of claim 1, wherein the grafted polytriallylamine is characterized by one or both of:
  an average adsorption of uric acid of about 1.0 mmol/g; and
  a glass transition temperature in a range of 85-95° C.

8. The grafted polytriallylamine of claim 1, wherein the mole percentage of the moiety to the tertiary amine is greater than 35% or in a range of 30% to 70%.

9. The grafted polytriallylamine of claim 8, wherein the mole percentage is about 50%.

10. A pharmaceutical composition comprising
  the grafted polytriallylamine of claim 1; and
  a pharmaceutically acceptable excipient, diluent, or carrier.

11. A method of treating a condition associated with an elevated serum uric acid level comprising administering to a subject in need thereof the pharmaceutical composition of claim 10.

12. The method of claim 11, satisfying one or more of:
  the grafted polytriallylamine binds to uric acid or precursor thereof;
  said condition is hyperuricemia or gout; or
  the pharmaceutical composition is administered orally.

13. A method of treating a condition associated with an elevated serum uric acid level comprising administering to a subject in need thereof the grafted polytriallylamine of claim 1.

14. The method of claim 13, satisfying one or more of:
  the grafted polytriallylamine binds to uric acid or precursor thereof;
  said condition is hyperuricemia or gout; or
  the grafted polytriallylamine is administered orally.

15. A method of making 4-N-(6-hexyl)-pyrimidine-2,4,6-triamine grafted polytriallylamine bicarbonate, comprising:
  (1) polymerizing triallylamine to yield polytriallylamine; and
  (2) reacting 4-N-(6-bromo-hexyl)-pyrimidine-2,4,6-triamine hydrobromide with the polytriallylamine at an elevated temperature.

16. The method of claim 15, wherein the polytriallylamine is synthesized according to a process comprising:
  (1) adding triallylamine to concentrated HCl at a temperature less than 15° C. to prepare hydrochloride triallylamine in an aqueous solution; and (2) mixing the hydrochloride triallylamine with 2,2'-Azobis(2-amidinopropane) dihydrochloride at an elevated temperature to yield polytriallylamine.

17. The method of claim 16, wherein the process satisfies one or more of the following conditions:
  the pH of the aqueous solution in step (1) is in a range of 2.6 to 3.1;
  the elevated temperature in step (2) is between 50° C. and 55° C.; or
  the process further comprises:
  (3) crushing the polytriallylamine into particles;
  (4) dispersing the particles into a mixture comprising methanol and NaOH at room temperature to yield a dispersion; and
  (5) filtering the dispersion to obtain a solid.

18. The method of claim 15, wherein the polytriallylamine is synthesized according to a process comprising:
  (1) adding triallylamine to concentrated HCl at a temperature less than 15° C. to prepare hydrochloride triallylamine in an aqueous solution;
  (2) mixing the hydrochloride triallylamine with 2,2'-Azobis(2-amidinopropane) dihydrochloride to obtain an aqueous phase; and
  (3) providing an organic phase to mix with the aqueous phase under nitrogen protection at an elevated temperature to yield polytriallylamine in a mixture.

19. The method of claim 18, wherein the process satisfies one or more of the following conditions:
  the pH of the aqueous solution in step (1) is in a range of 2.6 to 3.1;
  the elevated temperature in step (3) is between 55° C. and 65° C. or in a range of 80° C. and 85° C.;
  the organic phase comprises toluene and sorbitan monostearate (Span60); or
  the process further comprises: (4) filtering the mixture to obtain a solid of polytriallylamine.

20. A method of making a grafted polytriallylamine, comprising reacting an analog of pyrimidine-2,4-diamine with polytriallylamine, wherein the analog is selected from the group consisting of:

6-chloropyrimidine-2,4-diamine,

4-N-(6-bromo-hexyl)pyrimidine-2,4,6-triamine

N-(6-bromo-hexyl)pyrimidine-2,4,6-triamine

\* \* \* \* \*